United States Patent
Liu et al.

(10) Patent No.: US 12,280,133 B1
(45) Date of Patent: Apr. 22, 2025

(54) GLABRIDIN COMPOSITION WITH HIGH SKIN PERMEABILITY, AND PREPARATION METHOD AND USE THEREOF

(71) Applicants: Guangzhou Fanzhirong Cosmetics Co., Ltd., Guangzhou (CN); Guangzhou Qingnang Biotechnology Co., Ltd., Guangzhou (CN)

(72) Inventors: Haiyan Liu, Guangzhou (CN); Sen Hou, Guangzhou (CN); Anzhang Li, Guangzhou (CN); Tuzhen Yang, Guangzhou (CN); Jie Wei, Guangzhou (CN); Anning Wang, Guangzhou (CN)

(73) Assignees: Guangzhou Fanzhirong Cosmetics Co., Ltd., Guangzhou (CN); Guangzhou Qingnang Biotechnology Co., Ltd., Guangzhou (CN)

( * ) Notice: Subject to any disclaimer, the term of this patent is extended or adjusted under 35 U.S.C. 154(b) by 0 days.

(21) Appl. No.: 18/945,317

(22) Filed: Nov. 12, 2024

(30) Foreign Application Priority Data

Jul. 31, 2024 (CN) .......................... 202411035288.6

(51) Int. Cl.
| | |
|---|---|
| *A61K 8/49* | (2006.01) |
| *A61K 8/34* | (2006.01) |
| *A61K 8/37* | (2006.01) |
| *A61K 8/44* | (2006.01) |
| *A61K 8/67* | (2006.01) |
| *A61K 8/86* | (2006.01) |
| *A61Q 19/02* | (2006.01) |

(52) U.S. Cl.
CPC .............. *A61K 8/498* (2013.01); *A61K 8/345* (2013.01); *A61K 8/375* (2013.01); *A61K 8/44* (2013.01); *A61K 8/676* (2013.01); *A61K 8/86* (2013.01); *A61Q 19/02* (2013.01)

(58) Field of Classification Search
CPC ........ A61K 8/498; A61K 8/345; A61K 8/375; A61K 8/44; A61K 8/676; A61K 8/86; A61Q 19/02

See application file for complete search history.

(56) References Cited

U.S. PATENT DOCUMENTS

| 6,338,855 B1 | 1/2002 | Albacarys et al. |
| 2010/0062067 A1 | 3/2010 | Tonge et al. |

FOREIGN PATENT DOCUMENTS

| CN | 105193636 A | 12/2015 |
| CN | 116869846 A | 10/2023 |
| CN | 117064771 A | 11/2023 |

OTHER PUBLICATIONS

CN116869846A, Machine Translation (Year: 2023).*

* cited by examiner

*Primary Examiner* — Jeffrey S Lundgren
*Assistant Examiner* — Ibrahim D Bori
(74) *Attorney, Agent, or Firm* — Nitin Kaushik

(57) ABSTRACT

The present application provides a glabridin composition with high skin permeability and a preparation method and use thereof, belonging to the field of cosmetics. The glabridin composition is prepared from an S1 phase, an S2 phase and an S3 phase, in which the S1 phase consists of an oil and glabridin, the S2 phase is prepared from 3-o-ethyl ascorbic acid, an anionic surfactant, a nonionic surfactant, a polyol and water, and the S3 phase is water. The glabridin composition is prepared by conventional emulsifying equipment, and has low preparation cost, and simple operation process. The composition has good skin permeability, and has good state stability, good content stability, good pH stability and high mildness under high temperature and low temperature conditions, thus having unexpected technical effects.

10 Claims, No Drawings

GLABRIDIN COMPOSITION WITH HIGH SKIN PERMEABILITY, AND PREPARATION METHOD AND USE THEREOF

CROSS-REFERENCE TO RELATED APPLICATIONS

The application claims priority to Chinese patent application No. 2024110352886, filed on Jul. 31, 2024, the entire contents of which are incorporated herein by reference.

TECHNICAL FIELD

The present application relates to the field of cosmetics, in particular to a glabridin composition with high skin permeability and a preparation method and use thereof.

BACKGROUND

Glabridin, commonly known as "whitening gold", can effectively inhibit tyrosinase activity, dopachrome tautomerism, DHICA oxidase activity and cytochrome P450 3A4 enzyme (CYP3A4 for short) activity, thus achieving the purpose of whitening and spot removing efficiently and green. However, glabridin's insolubility in water and low permeability properties limit its application in formulas.

Glabridin is a fat-soluble active substance, which is soluble in polyols, slightly soluble in oils, and insoluble in water. Therefore, in order to enhance the skin penetration ability of glabridin, it is necessary to not only solve the problem of glabridin solubility, but also use carrier technologies such as microencapsulation, liposome and nanoemulsion to wrap the active ingredients, and carry glabridin to penetrate the stratum corneum of skin to enhance the permeability. However, according to the conventional preparation method and formula composition, there are technical problems such as low skin permeation rate, low glabridin solubility, poor stability, high irritation, high preparation cost and complicated operation.

The prior art provides methods for cyclodextrin inclusion of glabridin, such as preparing cyclodextrin inclusion complexes by technologies such as precipitation methods, grinding methods, freeze drying methods, and spray drying methods. These technologies require common equipment for non-cosmetic production, and the molecular weight of cyclodextrin is large and its outside is hydrophilic, thus greatly weakening the ability of active substances to directly penetrate the hydrophobic stratum corneum. In addition, in skin care product formulas, the cyclodextrin encapsulating system still has two disadvantages. One is that cyclodextrin itself is very sticky, which will make consumers feel an unpleasant sticky feeling during use. The other is that the cyclodextrin encapsulating system is susceptible to crystal precipitation in formulas. It is shown in some documents that polyols such as pentanediol and hexanediol will affect the encapsulating stability of cyclodextrin, which leads to difficulties for formulators in developing cosmetic formulas.

The prior art also provides methods for phospholipid inclusion of glabridin, which prepare phospholipid inclusion complexes by technologies such as film rehydration methods, reverse phase evaporation methods, injection methods, and microfluidic methods. These technologies also require common equipment for non-cosmetic production, and liposomes may aggregate, leak or change their structures during storage, resulting in the loss or early release of active substances, and phospholipases in vivo can decompose liposomes, which directly affects the delivery efficiency and controlled release properties of drugs.

Therefore, there is still an urgent need for a glabridin composition with high skin permeation rate, good solubility, good stability, good skin feeling, low irritation, low preparation cost and simple operation process.

SUMMARY

Overview of the Invention

In order to provide a glabridin composition with high skin permeation rate, good solubility, no crystal precipitation during stable placement, good content stability, good pH stability, high mildness, good skin feeling, low preparation cost and simple operation process, the present application provides the following technical schemes.

In a first aspect, the present application provides a glabridin composition prepared from an S1 phase, an S2 phase and an S3 phase, in which the S1 phase consists of an oil and glabridin, the S2 phase is prepared from 3-o-ethyl ascorbic acid, an anionic surfactant, a nonionic surfactant, a polyol and water, and the S3 phase is water;

the nonionic surfactant is oleth-20 and polyglycerol-10 oleate; the anionic surfactant is sodium stearoyl glutamate; the oil is caprylic acid/capric acid triglyceride; the polyol is 1,3-butanediol;

based on a total mass of the glabridin composition, the glabridin has a content of 0.10-4.00 wt %, and the 3-o-ethyl ascorbic acid has a content of 0.10-4.00 wt %; the nonionic surfactant has a total content of 0.70 wt %-10.00 wt %, and the oil has a content of 1.00 wt %-40.00 wt %; the polyol has a content of 0.60 wt %-6.00 wt %, the anionic surfactant has a content of 0.10 wt %-1.00 wt %, water in the S2 phase has a content of 0.30 wt %-3.00 wt %, and the balance is the S3 phase;

in addition, the present application also provides a preparation method of the glabridin composition.

The adoption of the technical schemes of the present application is beneficial to enhancing the skin permeability and solubility of the glabridin composition, and enhancing the state stability, content stability, pH stability and mildness of the composition under high temperature and low temperature conditions, thus having unexpected technical effects.

The adoption of the preparation method provided by the present application does not need to use common equipment for non-cosmetic production, and only uses simple process operations. It is beneficial to enhance the skin permeability and solubility of the glabridin composition, and to enhance its state stability, content stability, pH stability and mildness under high temperature and low temperature conditions.

In a second aspect, the present application provides use of the glabridin composition described in the first aspect in preparation of cosmetics.

In a third aspect, the present application provides a cosmetic, including the glabridin composition described in the first aspect.

DETAILED DESCRIPTION OF THE EMBODIMENTS

In order to solve the above technical problems, the present application provides a glabridin composition and a preparation method thereof.

In a first aspect, the present application provides a glabridin composition.

A glabridin composition, which is prepared from an S1 phase, an S2 phase and an S3 phase, in which the S1 phase consists of an oil and glabridin, the S2 phase is prepared from 3-o-ethyl ascorbic acid, an anionic surfactant, a nonionic surfactant, a polyol and water, and the S3 phase is water;

the nonionic surfactant is oleth-20 and polyglycerol-10 oleate;
the anionic surfactant is sodium stearoyl glutamate;
the oil is caprylic acid/capric acid triglyceride;
the polyol is 1,3-butanediol;
based on a total mass of the glabridin composition, the glabridin has a content of 0.10-4.00 wt %, and the 3-o-ethyl ascorbic acid has a content of 0.10-4.00 wt %; the nonionic surfactant has a total content of 0.70 wt %-10.00 wt %, and the oil has a content of 1.00 wt %-40.00 wt %; the polyol has a content of 0.60 wt %-6.00 wt %, the anionic surfactant has a content of 0.10 wt %-1.00 wt %, water in the S2 phase has a content of 0.30 wt %-3.00 wt %, and the balance is the S3 phase;
a preparation method of the glabridin composition comprises the following steps:
(1) mixing glabridin and the oil, heating for dissolution, and uniformly mixing to obtain the S1 phase;
(2) mixing 3-o-ethyl ascorbic acid, the anionic surfactant, the nonionic surfactant, the polyol and water, heating for dissolution, and uniformly mixing to obtain the S2 phase;
(3) adding the S1 phase obtained in the step (1) into the S2 phase obtained in the step (2) while stirring the S2 phase, and mixing, to form a gel; and
(4) then mixing the gel obtained in the step (3) with the S3 phase to obtain the glabridin composition.

In some examples, the oleth-20 has a content of 0.10 wt %-4.00 wt %, and the polyglycerol-10 oleate has a content of 0.60 wt %-6.00 wt %, based on the total mass of the glabridin composition.

In some examples, based on the total mass of the glabridin composition, the glabridin has a content of 1.00-4.00 wt %, and the 3-o-ethyl ascorbic acid has a content of 1.00-4.00 wt %; the oleth-20 has a total content of 0.50 wt %-4.00 wt %, the polyglycerol-10 oleate has a content of 6.00 wt %, and the oil has a content of 10.00 wt %-40.00 wt %; the polyol has a content of 6.00 wt %, the anionic surfactant has a content of 1.00 wt %, water in the S2 phase has a content of 3.00 wt %, and the balance is the S3 phase.

In some examples, based on the total mass of the glabridin composition, the glabridin has a content of 0.10 wt %, and the 3-o-ethyl ascorbic acid has a content of 0.10 wt %; the oleth-20 has a total content of 0.10 wt %, the polyglycerol-10 oleate has a content of 0.60 wt %, and the oil has a content of 1.00 wt %; the polyol has a content of 0.60 wt %, the anionic surfactant has a content of 0.10 wt %, water in the S2 phase has a content of 0.30 wt %, and the balance is the S3 phase.

In some examples, based on the total mass of the glabridin composition, the glabridin has a content of 1.00 wt %, and the 3-o-ethyl ascorbic acid has a content of 1.00 wt %; the oleth-20 has a total content of 0.50 wt % wt %, the polyglycerol-10 oleate has a content of 6.00 wt %, and the oil has a content of 10.00 wt %; the polyol has a content of 6.00 wt %, the anionic surfactant has a content of 1.00 wt %, water in the S2 phase has a content of 3.00 wt %, and the balance is the S3 phase.

In some examples, based on the total mass of the glabridin composition, the glabridin has a content of 1.00 wt %, and the 3-o-ethyl ascorbic acid has a content of 1.00 wt %; the oleth-20 has a total content of 1.00 wt %, the polyglycerol-10 oleate has a content of 6.00 wt %, and the oil has a content of 10.00 wt %; the polyol has a content of 6.00 wt %, the anionic surfactant has a content of 1.00 wt %, water in the S2 phase has a content of 3.00 wt %, and the balance is the S3 phase.

In some examples, based on the total mass of the glabridin composition, the glabridin has a content of 1.00 wt %, and the 3-o-ethyl ascorbic acid has a content of 2.00 wt %; the oleth-20 has a total content of 0.50 wt %, the polyglycerol-10 oleate has a content of 6.00 wt %, and the oil has a content of 10.00 wt %; the polyol has a content of 6.00 wt %, the anionic surfactant has a content of 1.00 wt %, water in the S2 phase has a content of 3.00 wt %, and the balance is the S3 phase.

In some examples, based on the total mass of the glabridin composition, the glabridin has a content of 2.00 wt %, and the 3-o-ethyl ascorbic acid has a content of 2.00 wt %; the oleth-20 has a total content of 2.00 wt %, the polyglycerol-10 oleate has a content of 6.00 wt %, and the oil has a content of 20.00 wt %; the polyol has a content of 6.00 wt %, the anionic surfactant has a content of 1.00 wt %, water in the S2 phase has a content of 3.00 wt %, and the balance is the S3 phase.

In some examples, based on the total mass of the glabridin composition, the glabridin has a content of 4.00 wt %, and the 3-o-ethyl ascorbic acid has a content of 4.00 wt %; the oleth-20 has a total content of 4.00 wt %, the polyglycerol-10 oleate has a content of 6.00 wt %, and the oil has a content of 40.00 wt %; the polyol has a content of 6.00 wt %, the anionic surfactant has a content of 1.00 wt %, water in the S2 phase has a content of 3.00 wt %, and the balance is the S3 phase.

In some examples, the heating for dissolution in the step (1) is heating to 60° C.-80° C. for dissolution. In some examples, the heating for dissolution in the step (1) is heating to 60° C., 65° C., 70° C., 75° C. or 80° C. for dissolution.

In some examples, the heating for dissolution in the step (2) is heating to 60° C.-70° C. for dissolution. In some examples, the heating for dissolution in the step (2) is heating to 60° C., 65° C. or 70° C. for dissolution.

In some examples, the heating for dissolution in the step (1) is heating to 70° C. for dissolution; and the heating for dissolution in the step (2) is heating to 60° C. for dissolution.

In some examples, the feeding mass ratio of water to the polyol in the step (2) is 1:1-1:2.

In a second aspect, the present application provides use of the glabridin composition described in the first aspect.

Use of the glabridin composition described in the first aspect in preparation of cosmetics.

In a third aspect, the present application provides a cosmetic.

A cosmetic, including the glabridin composition described in the first aspect.

In some examples, the cosmetic is an essence dosage form.

In some examples, the cosmetic is an essential dosage form, and includes an A phase, a B phase, a C phase, a D phase, a E phase and an F phase; the A phase includes water, EDTA disodium and carbomer; the B phase includes p-hydroxyacetophenone, 1,2-pentanediol and 1,2-hexanediol; the C phase includes water and arginine; the D phase includes hydrogenated lecithin, ethoxydiglycol, palmitoyl tripeptide-8 and alpha-tocopherol; the E phase includes glutathione and an aqueous plant extract solution; and the F phase is the glabridin composition described in the first aspect.

In some examples, the aqueous plant extract solution is an aqueous peony flower solution.

In some examples, based on the total mass of the cosmetic, the F phase has a content of 1.000 wt %-2.000 wt %; glutathione in the E phase has a content of 0.001 wt %-0.050 wt %; the aqueous peony flower solution in the E phase has a content of 0.050 wt %-0.500 wt %; hydrogenated lecithin in the D phase has a content of 0.040-0.100 wt %; ethoxydiglycol in the D phase has a content of 0.010 wt %-0.100 wt %; palmitoyl tripeptide-8 in the D phase has a content of 0.001 wt %-0.005 wt %; alpha-tocopherol in the D phase has a content of 0.005 wt %-0.010 wt %; water in the C phase has a content of 1.000 wt %-2.000 wt %; arginine in the C phase has a content of 0.100 wt %-0.500 wt %; p-hydroxyacetophenone in the B phase has a content of 0.050 wt %-0.300 wt %; 1,2-pentanediol in the B phase has a content of 1.000 wt %-5.000 wt %; 1,2-hexanediol in the B phase has a content of 0.500 wt %-1.000 wt %; EDTA disodium in the A phase has a content of 0.020 wt %-0.100 wt %; carbomer in the A phase has a content of 0.100 wt %-0.500 wt %; and the balance is water in the A phase.

In some examples, based on the total mass of the cosmetic, the F phase has a content of 1.000 wt %; glutathione in the E phase has a content of 0.010 wt %; the aqueous peony flower solution in the E phase has a content of 0.100 wt %; hydrogenated lecithin in the D phase has a content of 0.060 wt %; ethoxydiglycol in the D phase has a content of 0.020 wt %; palmitoyl tripeptide-8 in the D phase has a content of 0.002 wt %; alpha-tocopherol in the D phase has a content of 0.005 wt %; water in the C phase has a content of 1.000 wt %; arginine in the C phase has a content of 0.200 wt %; p-hydroxyacetophenone in the B phase has a content of 0.100 wt %; 1,2-pentanediol in the B phase has a content of 3.000 wt %; 1,2-hexanediol in the B phase has a content of 0.500 wt %; EDTA disodium in the A phase has a content of 0.050 wt %; carbomer in the A phase has a content of 0.200 wt %; and the balance is water in the A phase.

In some examples, based on the total mass of the cosmetic, the F phase has a content of 2.000 wt %; glutathione in the E phase has a content of 0.050 wt %; the aqueous peony flower solution in the E phase has a content of 0.500 wt %; hydrogenated lecithin in the D phase has a content of 0.100 wt %; ethoxydiglycol in the D phase has a content of 0.100 wt %; palmitoyl tripeptide-8 in the D phase has a content of 0.005 wt %; alpha-tocopherol in the D phase has a content of 0.010 wt %; water in the C phase has a content of 2.000 wt %; arginine in the C phase has a content of 0.500 wt %; p-hydroxyacetophenone in the B phase has a content of 0.300 wt %; 1,2-pentanediol in the B phase has a content of 5.000 wt %; 1,2-hexanediol in the B phase has a content of 1.000 wt %; EDTA disodium in the A phase has a content of 0.100 wt %; carbomer in the A phase has a content of 0.500 wt %; and the balance is water in the A phase.

In some examples, based on the total mass of the cosmetic, the F phase has a content of 1.000 wt %; glutathione in the E phase has a content of 0.001 wt %; the aqueous peony flower solution in the E phase has a content of 0.050 wt %; hydrogenated lecithin in the D phase has a content of 0.040 wt %; ethoxydiglycol in the D phase has a content of 0.010 wt %; palmitoyl tripeptide-8 in the D phase has a content of 0.001 wt %; alpha-tocopherol in the D phase has a content of 0.005 wt %; water in the C phase has a content of 1.000 wt %; arginine in the C phase has a content of 0.100 wt %; p-hydroxyacetophenone in the B phase has a content of 0.050 wt %; 1,2-pentanediol in the B phase has a content of 1.000 wt %; 1,2-hexanediol in the B phase has a content of 0.500 wt %; EDTA disodium in the A phase has a content of 0.020 wt %; carbomer in the A phase has a content of 0.100 wt %; and the balance is water in the A phase.

In some examples, the cosmetic is an essence dosage form, and the preparation method of the cosmetic includes:
(i) mixing each component of the A phase, heating for dissolution, and then cooling to 40° C.-50° C. to obtain the A phase;
(ii) mixing each component of the B phase, heating for dissolution, and then cooling to normal temperature to obtain the B phase;
(iii) stirring each component of the C phase until they are completely dissolved to obtain the C phase;
(iv) mixing and stirring each component of the D phase, heating to 65° C.-75° C., and homogenizing to obtain the D phase; and
(v) adding the B phase, the C phase, the D phase, the E phase and the F phase into the A phase obtained in the step (i) while stirring the A phase, and mixing, to obtain the cosmetic.

In some examples, the heating for dissolution in the step (i) is heating to 75-85° C. for 5-40 minutes, and stirring until they are completely dissolved. In some examples, the heating for dissolution in the step (i) is heating to 75° C., 80° C. or 85° C. for 5 minutes, 10 minutes, 15 minutes, 20 minutes, 25 minutes, 30 minutes, 35 minutes or 40 minutes, and stirring until they are completely dissolved.

In some examples, the cooling in the step (i) is cooling to 40° C., 41° C., 42° C., 43° C., 44° C., 45° C., 46° C., 47° C., 48° C., 49° C. or 50° C.

In some examples, the heating for dissolution in the step (ii) is heating to 60-70° C., and stirring until they are completely dissolved. In some examples, the heating for dissolution in the step (ii) is heating to 60° C., 61° C., 62° C., 63° C., 64° C., 65° C., 66° C., 67° C., 68° C., 69° C. or 70° C., and stirring until they are completely dissolved.

In some examples, the normal temperature in the step (ii) is 20° C.-35° C. In some examples, the normal temperature in the step (ii) is 25° C.-30° C.

In some examples, the heating to 65° C.-75° C. in the step (iv) is heating to 65° C., 66° C., 67° C., 68° C., 69° C., 70° C., 71° C., 72° C., 73° C., 74° C. and 75° C.

In some examples, the homogenization speed of the homogenization in the step (iv) is 1500 rpm-2500 rpm. In some examples, the homogenization speed of the homogenization in the step (iv) is 1500 rpm, 1600, 1700, 1800, 1900, 2000, 2100, 2200, 2300, 2400 或 2500 rpm.

In some examples, the time of the homogenization in the step (iv) is 5 minutes-30 minutes. In some examples, the time of the homogenization in the step (iv) is 5 minutes, 10 minutes, 15 minutes, 20 minutes, 25 minutes or 30 minutes.

Beneficial Effects

Compared with the prior art, the technical schemes provided by the present application have at least one beneficial technical effect as follows:
a) Compared with the formula lacking any component of 3-o-ethyl ascorbic acid, the polyol, the nonionic surfactant and the anionic surfactant, the glabridin composition with the formula provided by the present application is more beneficial to enhancing the permeability of the essence dosage form, thus having unexpected technical effects.

b) Compared with other preparation methods (for example, the addition sequence of 3-o-ethyl ascorbic acid is different), using the glabridin composition obtained by the preparation process provided by the present application is more beneficial to enhancing the permeability of the essence dosage form, thus having unexpected technical effects.
c) Compared with cyclodextrin inclusion and liposome inclusion, using the glabridin composition obtained by the preparation process provided by the present application is more beneficial to enhancing the permeability of the essence dosage form, thus having unexpected technical effects.
d) Compared with other nonionic surfactants, the glabridin composition obtained by using oleth-20 and polyglycerol-10 oleate as nonionic surfactants in the present application is more beneficial to enhancing the permeability of the essence dosage form, thus having unexpected technical effects.
e) Compared with other polyols, the glabridin composition obtained by using 1,3-butanediol as a polyol in the present application is more beneficial to enhancing the permeability of the essence dosage form, thus having unexpected technical effects.
f) Compared with other oils, the glabridin composition obtained by using caprylic acid/capric acid triglyceride as an oil in the present application is more beneficial to enhancing the permeability of the essence dosage form, thus having unexpected technical effects.
g) Compared with not adding 3-o-ethyl ascorbic acid, the glabridin composition with the formula provided by the present application is more beneficial to enhancing the onset rate and effect of the clinical whitening and spot removing efficacy of the essential dosage form, thus having unexpected technical effects.
h) Compared with other preparation methods (for example, the addition sequence of 3-o-ethyl ascorbic acid is different), using the glabridin composition obtained by the preparation process provided by the present application is more beneficial to enhancing the onset rate and effect of the clinical whitening and spot removing efficacy of the essential dosage form, thus having unexpected technical effects.
i) Compared with cyclodextrin inclusion and liposome inclusion, using the glabridin composition obtained by the preparation process provided by the present application is more beneficial to enhancing the onset rate and effect of the clinical whitening and spot removing efficacy of the essential dosage form, thus having unexpected technical effects.
j) Compared with the formula lacking any component of 3-o-ethyl ascorbic acid, the polyol, the nonionic surfactant and the anionic surfactant, using the formula provided by the present application is more beneficial to enhancing the state stability and content stability of the glabridin composition under high temperature and low temperature conditions.
k) Compared with other nonionic surfactants, using oleth-20 and polyglycerol-10 oleate in the present application is more beneficial to enhancing the state stability and content stability of the glabridin composition under high temperature and low temperature conditions.
l) Compared with other polyols, using 1,3-butanediol in the present application is more beneficial to enhancing the state stability and content stability of the glabridin composition under high temperature conditions.
m) Compared with other oils, using caprylic acid/capric acid triglyceride in the present application is more beneficial to enhancing the state stability and content stability of the glabridin composition under high temperature conditions.
n) Compared with other anionic surfactants, using sodium stearoyl glutamate in the present application is more beneficial to enhancing the state stability and content stability of the glabridin composition under high temperature and low temperature conditions.
o) Compared with other preparation methods (for example, the addition sequence of 3-o-ethyl ascorbic acid or the addition sequence of water is different), using the preparation process provided by the present application is more beneficial to enhancing the state stability and content stability of the glabridin composition under high temperature and low temperature conditions.
q) Compared with other preparation methods (for example, the addition sequence of 3-o-ethyl ascorbic acid is different), using the preparation process provided by the present application is more beneficial to enhancing the pH stability of the glabridin composition under high temperature and low temperature conditions.
q) Compared with not adding 3-o-ethyl ascorbic acid, the formula provided by the present application is more beneficial to enhancing the safety of the glabridin composition, thus having unexpected technical effects.
r) Compared with other preparation methods (for example, the addition sequence of 3-o-ethyl ascorbic acid is different), using the preparation process provided by the present application is more beneficial to enhancing the safety of the glabridin composition.
s) The preparation method of the glabridin composition provided by the present application is simple, need simple equipment which is all conventional equipment in the field of cosmetics, and does not need to use common equipment for non-cosmetic production, which is beneficial to reducing the preparation cost.

Terminology Description

In the foregoing description of the present application, all numbers disclosed herein are approximations, whether or not the words "approximately" or "about" are used. Based on the figures disclosed, there may be a difference of less than ±10% in the numerical value of each number or a reasonable difference considered by those in the field, such as a difference of ±1%, ±2%, ±3%, ±4% or ±5%.

The term "normal temperature" means the indoor ambient temperature, which is 20° C.-35° C., or 25° C.-30° C.

The term "and/or" should be understood to mean any one of the options or a combination of any two or more of the options.

The term "wt %" means mass percentage.

In the description of this specification, descriptions referring to the terms "an example", "some examples", "embodiments", "specific embodiments" or "some embodiments" and so on mean that specific characteristics, structures, materials or features described in connection with this example or embodiment are included in at least one example or embodiment of the present application. In this specification, the schematic expressions of the above terms are not necessarily aimed at the same example or embodiment. Moreover, the specific characteristics, structures, materials or features described may be combined in any one or more examples or embodiments in a suitable manner. In addition, those skilled in the art can associate and combine different examples or embodiments and characteristics of different examples or embodiments described in this specification without contradicting each other.

DETAILED DESCRIPTION

In order to make those skilled in the art better understand the technical schemes of the present application, some non-limiting examples are further disclosed below to further explain the present application in detail.

The reagents used in the present application can all be commercially available or can be prepared by the method described in the present application.

I. Test Method or Detection Method of Glabridin Content

For the test method of glabridin content, please refer to Q/FZR 0101-2023, Raw material for cosmetics-glabridin, wherein the chromatographic conditions are specifically as follows:

a) chromatographic column: ZORBAX StableBond C18, 4.6×250 mm, 5 um;
b) flow rate: 1.0 mL/min;
c) mobile phase: acetonitrile:water=80:20, filtered with a 0.22 μm membrane filter;
d) sample injection volume: 10 uL;
e) column temperature: 25° C.;
f) wavelength: 280 nm.

II. Reagent

Source of aqueous peony flower solution: product name: FangYe5031 Peony Hydrosols, purchased from "Shandong Fangye Biotechnology Co., Ltd.", batch number: 20231231B5031; INCI: aqueous peony (*PAEONIA SUFFRUTICOSA*) flower solution, p-hydroxyacetophenone, 1,2-hexanediol; wherein, the content of each component is: aqueous peony (*Paeonia suffruticosa*) flower solution 99%, p-hydroxyacetophenone 0.5% and 1,2-hexanediol 0.5%.

a) Example 1-Example 6: Preparation of Glabridin Composition b) Formula: See Table 1.

TABLE 1

| Split phases | Component | | Example 1 | Example 2 | Example 3 | Example 4 | Example 5 | Example 6 |
|---|---|---|---|---|---|---|---|---|
| S1 phase | oil | caprylic acid/capric acid triglyceride | 10.00 wt % | 10.00 wt % | 10.00 wt % | 20.00 wt % | 40.00 wt % | 1.00 wt % |
| | active ingredient | glabridin | 1.00 wt % | 1.00 wt % | 1.00 wt % | 2.00 wt % | 4.00 wt % | 0.10 wt % |
| S2 phase | 3-o-ethyl ascorbic acid | 3-o-ethyl ascorbic acid | 1.00 wt % | 1.00 wt % | 2.00 wt % | 2.00 wt % | 4.00 wt % | 0.10 wt % |
| | polyol | 1,3-butanediol | 6.00 wt % | 6.00 wt % | 6.00 wt % | 6.00 wt % | 6.00 wt % | 6.00 wt % |
| | nonionic surfactant | oleth-20 | 0.50 wt % | 1.00 wt % | 0.50 wt % | 2.00 wt % | 4.00 wt % | 0.10 wt % |
| | | polyglycerol-10 oleate | 6.00 wt % | 6.00 wt % | 6.00 wt % | 6.00 wt % | 6.00 wt % | 6.00 wt % |
| | anionic surfactant | sodium stearoyl glutamate | 1.00 wt % | 1.00 wt % | 1.00 wt % | 1.00 wt % | 1.00 wt % | 0.10 wt % |
| | water | water | 3.00 wt % | 3.00 wt % | 3.00 wt % | 3.00 wt % | 3.00 wt % | 0.30 wt % |
| S3 phase | water | water | balance | balance | balance | balance | balance | balance |

Preparation Method:

(1) Glabridin and the oil were mixed, heated to 70° C. for dissolution, and uniformly mixed to obtain the S1 phase;

(2) 3-o-ethyl ascorbic acid, the anionic surfactant, the nonionic surfactant, the polyol and water were mixed, heated to 60° C. for dissolution, and uniformly mixed to obtain the S2 phase;

(3) the S1 phase obtained in the step (1) was added into the S2 phase obtained in the step (2) while the S2 phase was stirred, and mixed, to form a gel; and (4) then the gel obtained in the step (3) was mixed with the S3 phase to obtain the glabridin composition.

Example 7-Example 11: Essence Dosage Form

Formula: See Table 2.

TABLE 2

Formula of essence dosage form

| Split phases | Component | Example 7 | Example 8 | Example 9 | Example 10 | Example 11 |
|---|---|---|---|---|---|---|
| A phase | water | balance | balance | balance | balance | balance |
| | EDTA disodium | 0.050 wt % | 0.050 wt % | 0.050 wt % | 0.100 wt % | 0.020 wt % |
| | carbomer | 0.200 wt % | 0.200 wt % | 0.200 wt % | 0.500 wt % | 0.100 wt % |
| B phase | p-hydroxy-acetophenone | 0.100 wt % | 0.100 wt % | 0.100 wt % | 0.300 wt % | 0.050 wt % |
| | 1,2-pentanediol | 3.000 wt % | 3.000 wt % | 3.000 wt % | 5.000 wt % | 1.000 wt % |
| | 1,2-hexanediol | 0.500 wt % | 0.500 wt % | 0.500 wt % | 1.000 wt % | 0.500 wt % |
| C phase | water | 1.000 wt % | 1.000 wt % | 1.000 wt % | 2.000 wt % | 1.000 wt % |
| | arginine | 0.200 wt % | 0.200 wt % | 0.200 wt % | 0.500 wt % | 0.100 wt % |
| D phase | hydrogenated lecithin | 0.060 wt % | 0.060 wt % | 0.060 wt % | 0.100 wt % | 0.040 wt % |
| | ethoxydiglycol | 0.020 wt % | 0.020 wt % | 0.020 wt % | 0.100 wt % | 0.010 wt % |
| | palmitoyl tripeptide-8 | 0.002 wt % | 0.002 wt % | 0.002 wt % | 0.005 wt % | 0.001 wt % |
| | alpha-tocopherol | 0.005 wt % | 0.005 wt % | 0.005 wt % | 0.010 wt % | 0.005 wt % |
| E phase | glutathione | 0.010 wt % | 0.010 wt % | 0.010 wt % | 0.050 wt % | 0.001 wt % |
| | aqueous peony flower solution | 0.100 wt % | 0.100 wt % | 0.100 wt % | 0.500 wt % | 0.050 wt % |
| F phase | / | glabridin composition obtained in Example 1: 1.000 wt % | glabridin composition obtained in Example 2: 1.000 wt % | glabridin composition obtained in Example 3: 1.000 wt % | glabridin composition obtained in Example 1: 2.000 wt % | glabridin composition obtained in Example 1: 1.000 wt % |

Preparation Method:

(1) Each component of the A phase was mixed, heated to 80° C. for 30 minutes, stirred until they were completely dissolved, and then cooled to 45° C. to obtain the A phase;

(2) each component of the B phase was mixed, heated to 65° C., stirred until they were completely dissolved, and then cooled to normal temperature to obtain the B phase;

(3) each component of the C phase was stirred until they were completely dissolved to obtain the C phase;

(4) each component of the D phase was mixed and stirred, heated to 70° C., and homogenized at 2000 rpm for 10 minutes to obtain the D phase; and (5) the B phase, the C phase, the D phase, the E phase and the F phase were added into the A phase obtained in the step (1) while the A phase was stirred, and mixed, to obtain the cosmetic product with the essence dosage form.

Comparative Example 1-Comparative Example 5: Glabridin Composition

Formula: See Table 3.

TABLE 3

Formulas of glabridin Compositions of Comparative Example 1-Comparative Example 5

| Split phases | | Component | Comparative Example 1 | Comparative Example 2 | Comparative Example 3 | Comparative Example 4 | Comparative Example 5 |
|---|---|---|---|---|---|---|---|
| S1 phase | oil | caprylic acid/capric acid triglyceride | 10.00 wt % | 10.00 wt % | 10.00 wt % | 10.00 wt % | 10.00 wt % |
| | active ingredient | glabridin | 1.00 wt % | 1.00 wt % | 1.00 wt % | 1.00 wt % | 1.00 wt % |
| S2 phase | 3-o-ethyl ascorbic acid | 3-o-ethyl ascorbic acid | 0 | 1.00 wt % | 1.00 wt % | 1.00 wt % | 1.00 wt % |
| | polyol | 1,3-butanediol | 6.00 wt % | 6.00 wt % | 6.00 wt % | 6.00 wt % | 0 |
| | nonionic surfactant | oleth-20 | 0.50 wt % | 0 | 6.50 wt % | 0.50 wt % | 0.50 wt % |
| | | polyglycerol-10 oleate | 6.00 wt % | 6.50 wt % | 0 | 7.00 wt % | 6.00 wt % |

TABLE 3-continued

Formulas of glabridin Compositions of Comparative Example 1-Comparative Example 5

| Split phases | Component | | Comparative Example 1 | Comparative Example 2 | Comparative Example 3 | Comparative Example 4 | Comparative Example 5 |
|---|---|---|---|---|---|---|---|
| | anionic surfactant | sodium stearoyl glutamate | 1.00 wt % | 1.00 wt % | 1.00 wt % | 0 | 1.00 wt % |
| | water | water | 3.00 wt % | 3.00 wt % | 3.00 wt % | 3.00 wt % | 3.00 wt % |
| S3 phase | water | water | balance | balance | balance | balance | balance |

Preparation method: The preparation was carried out according to the preparation method of Example 1, except that the component with the content of 0 was not added, and each of other components was added according to the content of the corresponding component in each comparative example.

Comparative Example 6-Comparative Example 11: Investigation of Nonionic Surfactant Formula: See Table 4.

TABLE 4

Investigation formula of nonionic surfactant

| Split phases | Component | | Comparative Example 6 | Comparative Example 7 | Comparative Example 8 | Comparative Example 9 | Comparative Example 10 | Comparative Example 11 |
|---|---|---|---|---|---|---|---|---|
| S1 phase | oil | caprylic acid/capric acid triglyceride | 10.00 wt % | 10.00 wt % | 10.00 wt % | 10.00 wt % | 10.00 wt % | 10.00 wt % |
| S2 phase | active ingredient | glabridin | 1.00 wt % | 1.00 wt % | 1.00 wt % | 1.00 wt % | 1.00 wt % | 1.00 wt % |
| | 3-o-ethyl ascorbic acid | 3-o-ethyl ascorbic acid | 1.00 wt % | 1.00 wt % | 1.00 wt % | 1.00 wt % | 1.00 wt % | 1.00 wt % |
| | polyol | 1,3-butanediol | 6.00 wt % | 6.00 wt % | 6.00 wt % | 6.00 wt % | 6.00 wt % | 6.00 wt % |
| | nonionic surfactant | oleth-20 | 0 | 0 | 0 | 0.50 wt % | 0.50 wt % | 0.50 wt % |
| | | polyglycerol-10 oleate | 6.00 wt % | 6.00 wt % | 6.00 wt % | 0 | 0 | 0 |
| | | polysorbate-80 | 0.50 wt % | 0 | 0 | 0 | 0 | 0 |
| | | sorbitan oleate | 0 | 0.50 wt % | 0 | 0 | 0 | 0 |
| | | mixture of polysorbate-80 and sorbitan oleate (mass ratio:10:3) | 0 | | 0.50 wt % | 0 | 0 | 0 |
| | | polyglycerol-10 stearate | 0 | 0 | 0 | 6.00 wt % | 0 | 0 |
| | | polyglycerol-10 myristate | 0 | 0 | 0 | 0 | 6.00 wt % | 0 |
| | | polyglycerol-10 dioleate | 0 | 0 | 0 | 0 | 0 | 6.00 wt % |
| | anionic surfactant | sodium stearoyl glutamate | 1.00 wt % | 1.00 wt % | 1.00 wt % | 1.00 wt % | 1.00 wt % | 1.00 wt % |
| | water | water | 3.00 wt % | 3.00 wt % | 3.00 wt % | 3.00 wt % | 3.00 wt % | 3.00 wt % |
| S3 phase | water | water | balance | balance | balance | balance | balance | balance |

Preparation method: The preparation was carried out according to the preparation method of Example 1, except that the component with the content of 0 was not added, and each of other components was selected according to the corresponding component in each comparative example and added according to the content of the corresponding component.

Comparative Example 12-Comparative Example 14: Investigation of Anionic Surfactant Formula: See Table 5.

TABLE 5

Investigation formula of anionic surfactant

| Split phases | Component | | Comparative Example 12 | Comparative Example 13 | Comparative Example 14 |
|---|---|---|---|---|---|
| S1 phase | oil | caprylic acid/capric acid triglyceride | 10.00 wt % | 10.00 wt % | 10.00 wt % |
| | active ingredient | glabridin | 1.00 wt % | 1.00 wt % | 1.00 wt % |
| S2 phase | 3-o-ethyl ascorbic acid | 3-o-ethyl ascorbic acid | 1.00 wt % | 1.00 wt % | 1.00 wt % |
| | polyol | 1,3-butanediol | 6.00 wt % | 6.00 wt % | 6.00 wt % |
| | nonionic surfactant | oleth-20 | 0.50 wt % | 0.50 wt % | 0.50 wt % |
| | | polyglycerol-10 oleate | 6.00 wt % | 6.00 wt % | 6.00 wt % |
| | anionic surfactant | potassium cetyl phosphate | 1.00 wt % | 0 | 0 |
| | | sodium di(lauramido glutamide) lysine | 0 | 1.00 wt % | 0 |
| | | tri(laureth-4)phosphate | 0 | 0 | 1.00 wt % |
| | water | water | 3.00 wt % | 3.00 wt % | 3.00 wt % |
| S3 phase | water | water | balance | balance | balance |

Preparation method: The preparation was carried out according to the preparation method of Example 1, except that different anionic surfactants were used.

Comparative Example 15-Comparative Example 18: Investigation of Oil

Formula: See Table 6.

TABLE 6

Investigation formula of oil

| Split phases | Component | | Comparative Example 15 | Comparative Example 16 | Comparative Example 17 | Comparative Example 18 |
|---|---|---|---|---|---|---|
| S1 phase | oil | olive oil | 10.00 wt % | 0 | 0 | 0 |
| | | castor oil | 0 | 10.00 wt % | 0 | 0 |
| | | hydrogenated polydecene | 0 | 0 | 10.00 wt % | 0 |
| | | phytosterol ester | 0 | 0 | 0 | 10.00 wt % |
| S2 phase | active ingredient | glabridin | 1.00 wt % | 1.00 wt % | 1.00 wt % | 1.00 wt % |
| | 3-o-ethyl ascorbic acid | 3-o-ethyl ascorbic acid | 1.00 wt % | 1.00 wt % | 1.00 wt % | 1.00 wt % |
| | polyol | 1,3-butane diol | 6.00 wt % | 6.00 wt % | 6.00 wt % | 6.00 wt % |
| | nonionic surfactant | oleth-20 | 0.50 wt % | 0.50 wt % | 0.50 wt % | 0.50 wt % |
| | | polyglycerol-10 oleate | 6.00 wt % | 6.00 wt % | 6.00 wt % | 6.00 wt % |
| | anionic surfactant | sodium stearoyl glutamate | 1.00 wt % | 1.00 wt % | 1.00 wt % | 1.00 wt % |
| | water | water | 3.00 wt % | 3.00 wt % | 3.00 wt % | 3.00 wt % |
| S3 phase | water | water | balance | balance | balance | balance |

Preparation method: The preparation was carried out according to the preparation method of Example 1, except that different oils were used.

Comparative Example 19-Comparative Example 21: Investigation of Polyol

Formula: See Table 7.

TABLE 7

Investigation formula of polyol

| Split phases | Component | | Comparative Example 19 | Comparative Example 20 | Comparative Example 21 |
|---|---|---|---|---|---|
| S1 phase | oil | caprylic acid/capric acid triglyceride | 10.00 wt % | 10.00 wt % | 10.00 wt % |
| | active ingredient | glabridin | 1.00 wt % | 1.00 wt % | 1.00 wt % |
| S2 phase | 3-o-ethyl ascorbic acid | 3-o-ethyl ascorbic acid | 1.00 wt % | 1.00 wt % | 1.00 wt % |
| | polyol | glycerol | 6.00 wt % | 0 | 0 |
| | | sorbitol | 0 | 6.00 wt % | 0 |
| | | 1,3-propanediol | 0 | 0 | 6.00 wt % |
| | nonionic surfactant | oleth-20 | 0.50 wt % | 0.50 wt % | 0.50 wt % |
| | | polyglycerol-10 oleate | 6.00 wt % | 6.00 wt % | 6.00 wt % |
| | anionic surfactant | sodium stearoyl glutamate | 1.00 wt % | 1.00 wt % | 1.00 wt % |
| | water | water | 3.00 wt % | 3.00 wt % | 3.00 wt % |
| S3 phase | water | water | balance | balance | balance |

Preparation method: The preparation was carried out according to the preparation method of Example 1, except that different polyols were used.

Comparative Example 22: Investigation of Preparation Method

The formula of this comparative example is shown in Table 8.

TABLE 8

Formula of Comparative Example 22

| Split phases | Component | | Comparative Example 22 |
|---|---|---|---|
| S1 phase | oil | caprylic acid/capric acid triglyceride | 10.00 wt % |
| | active ingredient | glabridin | 1.00 wt % |
| S2 phase | polyol | 1,3-butanediol | 6.00 wt % |
| | nonionic surfactant | oleth-20 | 0.50 wt % |
| | | polyglycerol-10 oleate | 6.00 wt % |
| | anionic surfactant | sodium stearoyl glutamate | 1.00 wt % |
| | water | water | 3.00 wt % |
| S3 phase | 3-o-ethyl ascorbic acid | 3-o-ethyl ascorbic acid | 1.00 wt % |
| | water | water | balance |

Preparation Method:

Compared with Example 1, this comparative example was different in that 3-o-ethyl ascorbic acid in the S1 phase was added in the step (4) in the preparation method, and the detailed steps were as follows:

(1) glabridin and the oil were mixed, heated to 70° C. for dissolution, and uniformly mixed to obtain the S1 phase;

(2) the nonionic surfactant, the anionic surfactant, the polyol and water were mixed, heated to 60° C. for dissolution, and uniformly mixed to obtain the S2 phase;

(3) the S1 phase obtained in the step (1) was added into the S2 phase obtained in the step (2) while the S2 phase was stirred, and mixed, to form a gel; and (4) then the gel obtained in the step (3) was mixed with water in the S3 phase and 3-o-ethyl ascorbic acid to obtain the glabridin composition.

Comparative Example 23: Investigation of Preparation Method

The formula of this comparative example is shown in Table 9.

TABLE 9

Formula of Comparative Example 23

| Split phases | Component | | Comparative Example 23 |
|---|---|---|---|
| S1 phase | oil | caprylic acid/capric acid triglyceride | 10.00 wt % |
| | active ingredient | glabridin | 1.00 wt % |
| S2 phase | polyol | 1,3-butanediol | 6.00 wt % |
| | nonionic surfactant | oleth-20 | 0.50 wt % |
| | | polyglycerol-10 oleate | 6.00 wt % |
| | anionic surfactant | sodium stearoyl glutamate | 1.00 wt % |
| | water | water | balance |
| S3 phase | 3-o-ethyl ascorbic acid | 3-o-ethyl ascorbic acid | 1.00 wt % |

Preparation Method:

Compared with the preparation method of Example 1, the preparation method of this comparative example was different in the feeding sequence of components in the preparation method, and the specific steps were as follows:

(1) glabridin and the oil were mixed, heated to 70° C. for dissolution, and uniformly mixed to obtain the S1 phase;

(2) the nonionic surfactant, the anionic surfactant, the polyol and water were mixed, heated to 60° C. for dissolution, and uniformly mixed to obtain the S2 phase;

(3) the S1 phase obtained in the step (1) was added into the S2 phase obtained in the step (2) while the S2 phase was stirred, and mixed, to obtain a mixture (note: no gel would be formed here); and (4) then the mixture obtained in the step (3) was mixed with 3-o-ethyl ascorbic acid to obtain the glabridin composition.

Comparative Example 24: Investigation of Cyclodextrin Dosage Form

TABLE 10

Formula of Comparative Example 24

| Split phases | Component | Addition amount |
| --- | --- | --- |
| S1 phase | 2-sulfobutyl-β-cyclodextrin | 4.50 wt % |
|  | water | 64.50 wt % |
| S2 phase | glabridin | 1.00 wt % |
|  | ethanol | 30.00 wt % |

Preparation Method:

The S1 phase was stirred until it was completely dissolved at normal temperature, and the S2 phase was stirred until it was completely dissolved at normal temperature; the S1 and S2 phases were mixed and shaken for 24 h at 200 r/min to obtain a clear and transparent solution; then, the solution was treated with a rotary evaporator at 45° C. to remove ethanol, and was further frozen in a refrigerator at −20° C. for 12 h, and then freeze-dried in a freeze dryer to prepare the glabridin composition (cyclodextrin dosage form) of Comparative Example 24.

Comparative Example 25: Investigation of Liposome Dosage Form

TABLE 11

Formula of Comparative Example 25

| Split phases | Component | Addition amount |
| --- | --- | --- |
| S1 phase | soybean phospholipid | 3.00 wt % |
|  | palmityl palmitate | 1.00 wt % |
|  | isopropyl myristate | 2.00 wt % |
|  | octyldodecanol | 2.00 wt % |
|  | glabridin | 2.00 wt % |
| S2 phase | vitamin E polyethylene glycol succinate | 1.00 wt % |
|  | 1,3-butanediol | 10.00 wt % |
|  | 1,3-propanediol | 5.00 wt % |
|  | water | 74.00 wt % |

Preparation Method:

The S1 phase was heated to 80° C. and stirred until it was completely dissolved, and the S2 phase was heated to 80° C. and stirred until it was completely dissolved; the S1 phase was added dropwise into the S2 phase, stirred continuously, sheared and emulsified at high speed of 10000 rpm for 1 min to prepare a micron dispersion; the micron dispersion was homogenized at high pressure and circulated for 5 times at 1500 bar to prepare the glabridin composition (in the dosage form of liposome) of Comparative Example 25.

Example 26-Example 50: Essence Dosage Form

Comparative Examples 1-25 were added to the formula of the essence dosage form, and the formula was shown in Table 12.

TABLE 12

Adding Comparative Examples 1-25 to formula of essence dosage form

| Split phases | Addition amount | Essence formulas of Comparative Example 26-Comparative Example 49 | Essence formula of Comparative Example 50 |
| --- | --- | --- | --- |
| A phase | water | balance | balance |
|  | EDTA disodium | 0.050 wt % | 0.050 wt % |
|  | carbomer | 0.200 wt % | 0.200 wt % |
| B phase | p-hydroxyacetophenone | 0.100 wt % | 0.100 wt % |
|  | 1,2-pentanediol | 3.000 wt % | 3.000 wt % |
|  | 1,2-hexanediol | 0.500 wt % | 0.500 wt % |
| C phase | water | 1.000 wt % | 1.000 wt % |
|  | arginine | 0.200 wt % | 0.200 wt % |
| D phase | hydrogenated lecithin | 0.060 wt % | 0.060 wt % |
|  | ethoxydiglycol | 0.020 wt % | 0.020 wt % |
|  | palmitoyl tripeptide-8 | 0.002 wt % | 0.002 wt % |
|  | alpha-tocopherol | 0.005 wt % | 0.005 wt % |
| E phase | glutathione | 0.010 wt % | 0.010 wt % |
|  | aqueous peony flower solution | 0.100 wt % | 0.100 wt % |
| F phase | / | glabridin compositions of Comparative Example 1-Comparative Example 24 (the glabridin compositions of Comparative Example 1-Comparative Example 24 were used correspondingly in turn in Comparative Example 26-Comparative Example): 1.000 wt % | glabridin composition obtained in Comparative Example 25: 0.500 wt % |

Preparation method: The preparation was carried out according to the preparation method of Examples 7-11, except that the F phase was replaced by the glabridin composition obtained in Comparative Example 1-Comparative Example 25, respectively, and the composition was added according to the component contents in Table 12.

Experimental Example 1: Permeability Experiment

Test Method:

(1) According to "GB-T27818-2011, Chemicals-testing method for skin absorption-in vitro" and "Q/FZR 0101-2023, Raw material for cosmetics-glabridin", the essence dosage forms of Example 7-Example 9 and Comparative Example 26, Comparative Example 47, Comparative Example 49 and Comparative Example 50 were used respectively to study the permeation behavior of the samples at 2 h, 4 h, 8 h, 12 h and 24 h based on the piglet skin-Franz cell system, as shown in Table 13.

(2) The essence dosage forms obtained in Comparative Example 27-Comparative Example 46 and Comparative Example 48 were used respectively to study the permeation behavior of the samples at 24 h based on the piglet skin-Franz cell system, as shown in Table 14.

In this experiment, three parallel groups were set up to obtain the average value. The test results are shown in Table 13 and Table 14.

TABLE 13

Investigation results of permeability at different Time/(ug/cm²)

Permeability (ug/cm²)

| Time point | Example 7 | Example 8 | Example 9 | Example 10 | Example 11 | Comparative Example 26 | Comparative Example 47 | Comparative Example 49 | Comparative Example 50 |
|---|---|---|---|---|---|---|---|---|---|
| 2 h | 25.08 | 28.11 | 30.05 | 50.34 | 26.25 | 12.65 | 15.45 | 10.76 | 18.96 |
| 4 h | 35.17 | 39.43 | 40.90 | 70.07 | 38.66 | 17.43 | 20.05 | 16.85 | 29.69 |
| 8 h | 51.81 | 55.55 | 62.25 | 99.31 | 52.30 | 24.78 | 28.64 | 20.68 | 35.78 |
| 12 h | 64.71 | 67.56 | 74.75 | 122.48 | 62.37 | 31.30 | 36.38 | 25.88 | 46.65 |
| 24 h | 85.22 | 95.69 | 104.87 | 170.55 | 92.85 | 45.12 | 53.79 | 37.73 | 62.37 |

TABLE 14

Investigation results of permeability at 24 h (ug/cm²)

| Sample | Comparative Example 27 | Comparative Example 28 | Comparative Example 29 | Comparative Example 30 | Comparative Example 31 | Comparative Example 32 | Comparative Example 33 |
|---|---|---|---|---|---|---|---|
| permeability at 24 h (ug/cm²) | 8.25 | 7.25 | 6.87 | 15.34 | 6.35 | 7.49 | 9.52 |

| Sample | Comparative Example 34 | Comparative Example 35 | Comparative Example 36 | Comparative Example 37 | Comparative Example 38 | Comparative Example 39 | Comparative Example 40 |
|---|---|---|---|---|---|---|---|
| permeability at 24 h (ug/cm²) | 28.67 | 35.53 | 40.74 | 45.90 | 46.90 | 48.79 | 48.55 |

| Sample | Comparative Example 41 | Comparative Example 42 | Comparative Example 43 | Comparative Example 44 | Comparative Example 45 | Comparative Example 46 | Comparative Example 47 |
|---|---|---|---|---|---|---|---|
| permeability at 24 h (ug/cm²) | 36.63 | 45.54 | 7.49 | 32.56 | 35.21 | 38.59 | 2.08 |

Conclusion (1) Compared with the formula lacking any component of 3-o-ethyl ascorbic acid, the polyol, the nonionic surfactant and the anionic surfactant, the glabridin composition with the formula provided by the present application is more beneficial to enhancing the permeability of the essence dosage form, thus having unexpected technical.

(2) Compared with other preparation methods (for example, the addition sequence of 3-o-ethyl ascorbic acid is different), using the glabridin composition obtained by the preparation process provided by the present application is more beneficial to enhancing the permeability of the essence dosage form, thus having unexpected technical effects.

(3) Compared with cyclodextrin inclusion and liposome inclusion, using the glabridin composition obtained by the preparation process provided by the present application is more beneficial to enhancing the permeability of the essence dosage form, thus having unexpected technical effects.

(4) Compared with other nonionic surfactants, the glabridin composition obtained by using oleth-20 and polyglycerol-10 oleate as nonionic surfactants in the present application is more beneficial to enhancing the permeability of the essence dosage form, thus having unexpected technical effects.

(5) Compared with other polyols, the glabridin composition obtained by using 1,3-butanediol as a polyol in the present application is more beneficial to enhancing the permeability of the essence dosage form, thus having unexpected technical effects.

(6) Compared with other oils, the glabridin composition obtained by using caprylic acid/capric acid triglyceride as an oil in the present application is more beneficial to enhancing the permeability of the essence dosage form, thus having unexpected technical effects.

Experimental Example 2: Verification of Clinical Whitening Efficacy

Test method: According to First method-test methods for whitening efficacy of human skin blackening model induced by ultraviolet rays, the essence dosage forms of Example 7-Example 9 and Comparative Example 26, Comparative Example 47, Comparative Example 49 and Comparative Example 50 were used respectively to see whether the difference of the skin color visual scores, the ITA° difference or the MI difference at any time point before and after application of the test product was significantly improved compared with the negative control ($P<0.05$), otherwise, it was considered that the test product has no spot removing and whitening efficacy. The test results are shown in Table 15.

TABLE 15

Results of differences before and after application of test products compared with negative control

| Parameter | After use | Example 7 | Example 8 | Example 9 | Example 10 | Example 11 | Comparative Example 26 | Comparative Example 47 | Comparative Example 48 | Comparative Example 50 |
|---|---|---|---|---|---|---|---|---|---|---|
| ΔITA° | 1 Week | 0.186 | 0.252 | 0.238 | 0.256 | 0.287 | 0.245 | 0.316 | 0.252 | 0.276 |
|  | 2 Week | 0.012 | 0.046 | 0.026 | 0.005 | 0.041 | 0.258 | 0.250 | 0.273 | 0.248 |
|  | 3 Week | 0.008 | 0.012 | 0.013 | 0.002 | 0.010 | 0.165 | 0.157 | 0.184 | 0.110 |
|  | 4 Week | 0.002 | 0.006 | 0.005 | 0.002 | 0.005 | 0.038 | 0.018 | 0.071 | 0.044 |
| ΔMI | 1 Week | 0.249 | 0.354 | 0.295 | 0.346 | 0.326 | 0.325 | 0.368 | 0.317 | 0.298 |
|  | 2 Week | 0.215 | 0.268 | 0.249 | 0.195 | 0.246 | 0.287 | 0.265 | 0.275 | 0.286 |
|  | 3 Week | 0.036 | 0.166 | 0.133 | 0.024 | 0.153 | 0.225 | 0.180 | 0.197 | 0.198 |
|  | 4 Week | 0.012 | 0.035 | 0.032 | 0.009 | 0.021 | 0.065 | 0.051 | 0.096 | 0.049 |
| Δ skin color or visual score | 1 Week | 0.354 | 0.345 | 0.389 | 0.368 | 0.340 | 0.369 | 0.380 | 0.360 | 0.365 |
|  | 2 Week | 0.222 | 0.233 | 0.297 | 0.196 | 0.254 | 0.298 | 0.305 | 0.275 | 0.287 |
|  | 3 Week | 0.168 | 0.126 | 0.154 | 0.102 | 0.131 | 0.224 | 0.198 | 0.168 | 0.175 |
|  | 4 Week | 0.041 | 0.037 | 0.047 | 0.011 | 0.045 | 0.105 | 0.080 | 0.102 | 0.050 |

Conclusion (1) Compared with not adding 3-o-ethyl ascorbic acid, the glabridin composition with the formula provided by the present application is more beneficial to enhancing the onset rate and effect of the clinical whitening and spot removing efficacy of the essential dosage form, thus having unexpected technical effects.

(2) Compared with other preparation methods (for example, the addition sequence of 3-o-ethyl ascorbic acid is different), using the glabridin composition obtained by the preparation process provided by the present application is more beneficial to enhancing the onset rate and effect of the clinical whitening and spot removing efficacy of the essential dosage form, thus having unexpected technical effects.

(3) Compared with cyclodextrin inclusion and liposome inclusion, using the glabridin composition obtained by the preparation process provided by the present application is more beneficial to enhancing the onset rate and effect of the clinical whitening and spot removing efficacy of the essential dosage form, thus having unexpected technical effects.

Experimental Example 3: Investigation of State Stability and Content Stability

Test method: According to ISO/TR 18811-2018, Cosmetics-Guidelines on the stability testing of cosmetic products and Q/FZR 0101-2023, Raw material for cosmetics-glabridin, the glabridin compositions prepared in the above examples and comparative examples were respectively placed at 45±2° C. and −15±2° C. to observe the state stability for 6 months and test the glabridin content after 6 months (the content here represented the ratio of the measured concentration of glabridin in the product to the theoretical concentration multiplied by 100%) (the sampling and detecting time points include 0 day, 7 days, 14 days, 1 month, 3 months and 6 months). The results are shown in Table 16, Table 17 and Table 18. (Note: 1. Stop observing immediately when there is abnormal stability performance of crystal precipitation or delamination, and "/" means that the stability is not observed; 2. The content of samples with crystal precipitation observed by naked eyes will be no longer tested)

TABLE 16

State stability at 45 ± 2° C. for 6 months

| Group | 0 days | 7 days | 14 days | 1 month | 3 months | 6 months |
|---|---|---|---|---|---|---|
| Example 1 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |

TABLE 16-continued

| | State stability at 45 ± 2° C. for 6 months | | | | | |
|---|---|---|---|---|---|---|
| Group | 0 days | 7 days | 14 days | 1 month | 3 months | 6 months |
| Example 2 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |
| Example 3 | no precipitation and no delamination | no discoloration, no precipitation and no delamination | no discoloration, no precipitation and no delamination | no discoloration, no precipitation and no delamination | no discoloration, no precipitation and no delamination | slight discoloration, no precipitation and no delamination |
| Example 4 | no precipitation and no delamination | no discoloration, no precipitation and no delamination | no discoloration, no precipitation and no delamination | no discoloration, no precipitation and no delamination | no discoloration, no precipitation and no delamination | slight discoloration, no precipitation and no delamination |
| Example 5 | no precipitation and no delamination | no discoloration, no precipitation and no delamination | no discoloration, no precipitation and no delamination | no discoloration, no precipitation and no delamination | no discoloration, no precipitation and no delamination | slight discoloration, no precipitation and no delamination |
| Example 6 | no precipitation and no delamination | no discoloration, no precipitation and no delamination | no discoloration, no precipitation and no delamination | no discoloration, no precipitation and no delamination | no discoloration, no precipitation and no delamination | slight discoloration, no precipitation and no delamination |
| Comparative Example 1 | no precipitation and no delamination | no discoloration, no precipitation and no delamination | slight discoloration, no precipitation and no delamination | slight discoloration, no precipitation and no delamination | obvious discoloration, no precipitation and no delamination | obvious discoloration, no precipitation and no delamination |
| Comparative Example 2 | crystal precipitation and no delamination | / | / | / | / | / |
| Comparative Example 3 | crystal precipitation and delamination | / | / | / | / | / |
| Comparative Example 4 | crystal precipitation and delamination | / | / | / | / | / |
| Comparative Example 5 | no precipitation and no delamination | no discoloration no precipitation and slight delamination | / | / | / | / |
| Comparative Example 6 | crystal precipitation and no delamination | / | / | / | / | / |
| Comparative Example 7 | crystal precipitation and no delamination | / | / | / | / | / |
| Comparative Example 8 | crystal precipitation and no delamination | / | / | / | / | / |
| Comparative Example 9 | no precipitation and no delamination | no discoloration, no precipitation and no delamination | no discoloration, no precipitation and no delamination | no discoloration, crystal precipitation and slight delamination | / | / |

TABLE 16-continued

| | State stability at 45 ± 2° C. for 6 months | | | | | |
|---|---|---|---|---|---|---|
| Group | 0 days | 7 days | 14 days | 1 month | 3 months | 6 months |
| Comparative Example 10 | no precipitation and no delamination | no discoloration, no precipitation and no delamination | no discoloration, no precipitation and slight delamination | / | / | / |
| Comparative Example 11 | no precipitation and no delamination | no discoloration, no precipitation and no delamination | no discoloration, no precipitation and no delamination | no discoloration, no precipitation and no delamination | slight discoloration, no precipitation and slight delamination | / |
| Comparative Example 12 | no precipitation and no delamination | no discoloration, no precipitation and no delamination | no discoloration, no precipitation and no delamination | no discoloration, no precipitation and no delamination | no discoloration, no precipitation and no delamination | no discoloration, crystal precipitation and slight delamination |
| Comparative Example 13 | no precipitation and no delamination | no discoloration, no precipitation and no delamination | no discoloration, no precipitation and no delamination | no discoloration, crystal precipitation and slight delamination | / | / |
| Comparative Example 14 | no precipitation and no delamination | crystal precipitation and slight delamination | / | / | / | / |
| Comparative Example 15 | no precipitation and no delamination | slight discoloration, no precipitation and no delamination | obvious discoloration, no precipitation and no delamination | severe discoloration and taste change, no precipitation and no delamination | severe discoloration and taste change, no precipitation and no delamination | severe discoloration, slight precipitation and no delamination |
| Comparative Example 16 | no precipitation and no delamination | slight crystal precipitation and no delamination | / | / | / | / |
| Comparative Example 17 | no precipitation and no delamination | no precipitation and no delamination | no precipitation and no delamination | no precipitation and no delamination | no precipitation and no delamination | no precipitation and slight delamination |
| Comparative Example 18 | crystal precipitation and no delamination | / | / | / | / | / |
| Comparative Example 19 | no precipitation and no delamination | no precipitation and slight delamination | / | / | / | / |
| Comparative Example 20 | no precipitation and no delamination | no precipitation and no delamination | no precipitation and slight delamination | / | / | / |
| Comparative Example 21 | no precipitation and no delamination | no precipitation and no delamination | / | / | / | / |
| Comparative Example 22 | no precipitation and no delamination | no precipitation and no delamination | no discoloration, no precipitation and no delamination | no discoloration, no precipitation and no delamination | slight discoloration, no precipitation and no delamination | slight discoloration, no precipitation and no delamination |
| Comparative Example 23 | precipitation and delamination | / | / | / | / | / |
| Comparative Example 24 | no precipitation and no delamination | no discoloration, no precipitation and no delamination | slight discoloration, no precipitation and no delamination | slight discoloration, no precipitation and no delamination | obvious discoloration, no precipitation and no delamination | severe discoloration, no precipitation and no delamination |

TABLE 16-continued

| Group | State stability at 45 ± 2° C. for 6 months | | | | | |
|---|---|---|---|---|---|---|
| | 0 days | 7 days | 14 days | 1 month | 3 months | 6 months |
| Comparative Example 25 | no precipitation and no delamination | no discoloration, no precipitation and no delamination | no discoloration, no precipitation and no delamination | slight discoloration, no precipitation and no delamination | slight discoloration, no precipitation and no delamination | obvious discoloration, no precipitation and no delamination |

TABLE 17

| Group | State stability at −15 ± 2° C. for 6 months | | | | | |
|---|---|---|---|---|---|---|
| | 0 days | 7 days | 14 days | 1 month | 3 months | 6 months |
| Example 1 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |
| Example 2 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |
| Example 3 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |
| Example 4 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |
| Example 5 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |
| Example 6 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |
| Comparative Example 1 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |
| Comparative Example 2 | crystal precipitation and no delamination | / | / | / | / | / |
| Comparative Example 3 | crystal precipitation and delamination | / | / | / | / | / |
| Comparative Example 4 | crystal precipitation and delamination | / | / | / | / | / |
| Comparative Example 5 | no precipitation and no delamination | crystal precipitation and delamination | / | / | / | / |

TABLE 17-continued

| | State stability at −15 ± 2° C. for 6 months | | | | | |
|---|---|---|---|---|---|---|
| Group | 0 days | 7 days | 14 days | 1 month | 3 months | 6 months |
| Comparative Example 6 | crystal precipitation and no delamination | / | / | / | / | / |
| Comparative Example 7 | crystal precipitation and no delamination | / | / | / | / | / |
| Comparative Example 8 | crystal precipitation and no delamination | / | / | / | / | / |
| Comparative Example 9 | no precipitation and no delamination | no discoloration, no precipitation and no delamination | no discoloration, no precipitation and no delamination | crystal precipitation and no delamination | / | / |
| Comparative Example 10 | no precipitation and no delamination | no discoloration, no precipitation and no delamination | no discoloration, crystal precipitation and no delamination | / | / | / |
| Comparative Example 11 | no precipitation and no delamination | no discoloration, no precipitation and no delamination | no discoloration, no precipitation and no delamination | no discoloration, no precipitation and no delamination | slight discoloration and no precipitation | / |
| Comparative Example 12 | no precipitation and no delamination | no discoloration, no precipitation and no delamination | no discoloration, no precipitation and no delamination | no discoloration, no precipitation and no delamination | no discoloration, no precipitation and no delamination | no discoloration and slight crystal precipitation |
| Comparative Example 13 | no precipitation and no delamination | no discoloration, no precipitation and no delamination | no discoloration, no precipitation and no delamination | no discoloration, no precipitation and no delamination | / | / |
| Comparative Example 14 | no precipitation and no delamination | crystal precipitation and no delamination | / | / | / | / |
| Comparative Example 15 | no precipitation and no delamination | no discoloration, no precipitation and no delamination | no discoloration, no precipitation and no delamination | no discoloration and taste change, no precipitation and no delamination | slight discoloration and taste change, no precipitation and no delamination | slight discoloration, slight precipitation and no delamination |
| Comparative Example 16 | no precipitation and no delamination | slight precipitation and no delamination | / | / | / | / |
| Comparative Example 17 | no precipitation and no delamination | no discoloration, no precipitation and no delamination | no discoloration, no precipitation and no delamination | no discoloration, no precipitation and no delamination | no discoloration, no precipitation and no delamination | no discoloration, obvious crystal precipitation and slight delamination |
| Comparative Example 18 | crystal precipitation and no delamination | / | / | / | / | / |
| Comparative Example 19 | no precipitation and no delamination | no discoloration, no precipitation and no delamination | / | / | / | / |

TABLE 17-continued

State stability at −15 ± 2° C. for 6 months

| Group | 0 days | 7 days | 14 days | 1 month | 3 months | 6 months |
|---|---|---|---|---|---|---|
| Comparative Example 20 | no precipitation and no delamination | no discoloration, no precipitation and no delamination | no discoloration, no precipitation and no delamination | / | / | / |
| Comparative Example 21 | no precipitation and no delamination | slight crystal precipitation and no delamination | / | / | / | / |
| Comparative Example 22 | no precipitation and no delamination | no discoloration, no precipitation and no delamination | no discoloration, no precipitation and no delamination | no discoloration, no precipitation and no delamination | no discoloration, no precipitation and no delamination | no discoloration, no precipitation and no delamination |
| Comparative Example 23 | precipitation and delamination | / | / | / | / | / |
| Comparative Example 24 | no precipitation and no delamination | no discoloration, no precipitation and no delamination | no discoloration, no precipitation and no delamination | no discoloration, no precipitation and no delamination | no discoloration, no precipitation and no delamination | slight discoloration, no precipitation and no delamination |
| Comparative Example 25 | no precipitation and no delamination | no precipitation and no delamination | no precipitation and no delamination | no precipitation and no delamination | no precipitation and no delamination | no precipitation and no delamination |

TABLE 18

Content stability

| Group | 0 days | 45 ± 2° C. for 6 months | −15 ± 2° C. for 6 months |
|---|---|---|---|
| Example 1 | 95% | 89% | 94% |
| Example 2 | 95% | 90% | 95% |
| Example 3 | 94% | 92% | 94% |
| Example 4 | 95% | 92% | 95% |
| Example 5 | 96% | 93% | 95% |
| Example 6 | 93% | 90% | 92% |
| Comparative Example 1 | 94% | 75% | 92% |
| Comparative Example 11 | 94% | 73% | 86% |
| Comparative Example 12 | 93% | 64% | 63% |
| Comparative Example 13 | 95% | 55% | 92% |
| Comparative Example 17 | 95% | 87% | 42% |
| Comparative Example 22 | 94% | 81% | 93% |
| Comparative Example 24 | 91% | 72% | 87% |
| Comparative Example 25 | 93% | 85% | 92% |

Conclusion (1) Compared with the formula lacking any component of 3-o-ethyl ascorbic acid, the polyol, the nonionic surfactant and the anionic surfactant, using the formula provided by the present application is more beneficial to enhancing the state stability and content stability of the glabridin composition under high temperature and low temperature conditions.

(2) Compared with other nonionic surfactants, using oleth-20 and polyglycerol-10 oleate in the present application is more beneficial to enhancing the state stability and content stability of the glabridin composition under high temperature and low temperature conditions.

(3) Compared with other polyols, using 1,3-butanediol in the present application is more beneficial to enhancing the state stability and content stability of the glabridin composition under high temperature conditions.

(4) Compared with other oils, using caprylic acid/capric acid triglyceride in the present application is more beneficial to enhancing the state stability and content stability of the glabridin composition under high temperature conditions.

(5) Compared with other anionic surfactants, using sodium stearoyl glutamate in the present application is more beneficial to enhancing the state stability and content stability of the glabridin composition under high temperature and low temperature conditions.

(6) Compared with other preparation methods (for example, the addition sequence of 3-o-ethyl ascorbic acid or the addition sequence of water is different), using the preparation process provided by the present application is more beneficial to enhancing the state stability and content stability of the glabridin composition under high temperature and low temperature conditions.

Experimental Example 4: Investigation of pH Stability

Test method: According to "GB/T 13531.1-2008, General methods on determination of cosmetics-determination of pH", the glabridin compositions with high skin permeation, penetration-promoting and water solubility prepared in Examples 1-6, Comparative Example 1 and Comparative Example 22 were used respectively to determine the pH at each stable placement time point (see Experimental Example 3 for stable placement conditions and time), and test the pH stability of the samples. The results are shown in Table 19.

TABLE 19

Investigation results of pH stability

| Group | 0 days normal temperature | 7 days 45° C. | 7 days −15° C. | 14 days 45° C. | 14 days −15° C. | 1 month 45° C. | 1 month −15° C. | 3 months 45° C. | 3 months −15° C. | 6 months 45° C. | 6 months −15° C. |
|---|---|---|---|---|---|---|---|---|---|---|---|
| Example 1 | 5.61 | 5.59 | 5.60 | 5.56 | 5.58 | 5.52 | 5.57 | 5.41 | 5.49 | 5.26 | 5.42 |
| Example 2 | 5.54 | 5.52 | 5.55 | 5.51 | 5.51 | 5.46 | 5.51 | 5.35 | 5.40 | 5.24 | 5.35 |
| Example 3 | 5.58 | 5.55 | 5.56 | 5.50 | 5.54 | 5.42 | 5.53 | 5.26 | 5.43 | 5.11 | 5.39 |
| Example 4 | 5.72 | 5.68 | 5.72 | 5.64 | 5.71 | 5.52 | 5.69 | 5.43 | 5.53 | 5.32 | 5.40 |
| Example 5 | 5.62 | 5.58 | 5.61 | 5.50 | 5.59 | 5.42 | 5.58 | 5.26 | 5.47 | 4.85 | 5.38 |
| Example 6 | 5.68 | 5.64 | 5.65 | 5.60 | 5.64 | 5.56 | 5.62 | 5.50 | 5.52 | 5.23 | 5.46 |
| Comparative Example 1 | 5.66 | 5.60 | 5.64 | 5.58 | 5.62 | 5.55 | 5.58 | 5.48 | 5.52 | 5.34 | 5.44 |
| Comparative Example 22 | 5.58 | 5.42 | 5.52 | 5.25 | 5.48 | 4.91 | 5.30 | 4.54 | 5.10 | 4.21 | 4.86 |

Conclusion: According to Examples 1-6 and Comparative Example 22, compared with other preparation methods (for example, the addition sequence of 3-o-ethyl ascorbic acid is different), using the preparation process provided by the present application is more beneficial to enhancing the pH stability of the glabridin composition under high temperature and low temperature conditions.

Experimental Example 5: Patch Experiment

Test method: According to "Safety and technical standards for cosmetics (2015 Edition)-Human skin patch experiment", glabridin compositions of Examples 1-6 and Comparative Example 1 and Comparative Example 22 were used respectively to carry out the skin patch test (wherein the test samples were samples stored for 0 days, at 45° C. for 6 months and at −15° C. for 6 months respectively).
Test scoring criteria: See Table 20.
Test result: See Table 21.

TABLE 20

Scoring criteria

| Ranking | Degree of reaction | Skin reaction |
|---|---|---|
| 0 | − | negative reaction |
| 1 | ± | suspicious reaction: only faint erythema |
| 2 | + | weak positive reaction: erythema, infiltration, edema and possibly papules |
| 3 | ++ | strong positive reaction: erythema, infiltration, edema, papules, herpes; the reaction may be beyond the test area |
| 4 | +++ | very strong positive reaction: obvious erythema, severe infiltration, edema, fusion herpes; the reaction is beyond the test area |

TABLE 21

Test results

| Group | 0 days | Patch ranking 45° C. for 6 months | −15° C. for 6 months |
|---|---|---|---|
| Example 1 | 0 | 0 | 0 |
| Example 2 | 0 | 0 | 0 |
| Example 3 | 0 | 0 | 0 |
| Example 4 | 0 | 0 | 0 |
| Example 5 | 0 | 0 | 0 |
| Example 6 | 0 | 0 | 0 |
| Comparative Example 1 | 0 | 2 | 1 |
| Comparative Example 22 | 0 | 3 | 2 |

Conclusion (1) Compared with not adding 3-o-ethyl ascorbic acid, the formula provided by the present application is more beneficial to enhancing the safety of the glabridin composition, thus having unexpected technical effects.

(2) Compared with other preparation methods (for example, the addition sequence of 3-o-ethyl ascorbic acid is different), using the preparation process provided by the present application is more beneficial to enhancing the safety of the glabridin composition.

The method of the present application has been described through preferred examples, and relevant personnel can obviously modify or appropriately modify and combine the method and use described herein within the content, spirit and scope of the present application to achieve and apply the technology of the present application. Those skilled in the art can learn from the contents herein, and improve the process parameters appropriately to achieve the present application. It is particularly important to point out that all similar substitutions and modifications are obvious to those skilled in the art, and they are all considered to be included in the present application.

What is claimed is:
1. A glabridin composition prepared from:
A) an S1 phase consisting of an oil and glabridin;
B) an S2 phase consisting 3-O-ethyl ascorbic acid, an anionic surfactant, a nonionic surfactant, a polyol and water; and
C) water as an S3 phase,
wherein:
the nonionic surfactant is oleth-20 and polyglycerol-10-oleate;

the oil is caprylic acid/capric acid triglyceride;
the polyol is 1,3-butanediol; and
the anionic surfactant is sodium stearoyl glutamate,
and based on a total mass, the glabridin composition comprises:
 0.10-4.00 wt % glabridin;
 0.10-4.00 wt % 3-O-ethyl ascorbic acid;
 0.70-10.00 wt % nonionic surfactant;
 1.00-40.00 wt % oil;
 0.60-6.00 wt % polyol;
 0.10-1.00 wt % anionic surfactant;
 0.30-3.00 wt % water in the S2 phase; and
 balance is S3 phase.

2. The glabridin composition according to claim 1, wherein the composition comprises 0.10-4.00 wt % oleth-20 and 0.60-6.00 wt % polyglycerol-10-oleate.

3. The glabridin composition according to claim 1, wherein the composition comprises:
 1.00-4.00 wt % glabridin;
 1.00-4.00 wt % 3-O-ethyl ascorbic acid;
 0.50-4.00 wt % oleth-20;
 6.00 wt % polyglycerol-10-oleate;
 10.00-40.00 wt % oil;
 6.00 wt % polyol;
 1.00 wt % anionic surfactant;
 3.00 wt % water in the S2 phase; and
 balance is S3 phase.

4. The glabridin composition according to claim 1, wherein the composition comprises:
 1.00 wt % glabridin;
 1.00 wt % 3-O-ethyl ascorbic acid;
 0.50 wt % oleth-20;
 6.00 wt % polyglycerol-10-oleate;
 10.00 wt % oil;
 6.00 wt % polyol;
 1.00 wt % anionic surfactant;
 3.00 wt % water in the S2 phase; and
 balance is S3 phase.

5. A cosmetic, comprising the glabridin composition according to claim 1.

6. A method for the preparation of a glabridin composition according to claim 1 comprising:
 (1) mixing glabridin and the oil under heating to obtain the S1 phase;
 (2) mixing 3-O-ethyl ascorbic acid, the anionic surfactant, the nonionic surfactant, the polyol and water, under heating to obtain the S2 phase;
 (3) adding the S1 phase obtained in the step (1) into the S2 phase obtained in step (2), under stirring to form a gel; and
 (4) mixing the gel obtained in step (3) with the S3 phase to obtain the glabridin composition.

7. The method according to claim 6, wherein the heating in step (1) is carried out at 60° C.-80° C.

8. The method according to claim 6, wherein the heating in step (2) is carried out at 60° C.-70° C.

9. The method according to claim 6, wherein the heating in step (1) is carried out at 70° C.; and the heating in step (2) is carried out at 60° C.

10. The method according to claim 6, wherein the ratio of water to the polyol is 1:1-1:2.

* * * * *